United States Patent [19]

Takeshita

[11] 4,453,919
[45] Jun. 12, 1984

[54] DENTAL SCALER

[75] Inventor: Saburou Takeshita, Tokyo, Japan

[73] Assignee: Micron Co., Ltd., Tokyo, Japan

[21] Appl. No.: 368,057

[22] Filed: Apr. 13, 1982

[30] Foreign Application Priority Data

| Apr. 24, 1981 | [JP] | Japan | 56-62049 |
| Oct. 1, 1981 | [JP] | Japan | 56-146526[U] |
| Oct. 22, 1981 | [JP] | Japan | 56-158192[U] |

[51] Int. Cl.$^3$ ............................ A61C 1/07; A61C 3/03
[52] U.S. Cl. ................................................. 433/120
[58] Field of Search ................ 433/120, 118; 366/124, 366/125, 126

[56] References Cited

U.S. PATENT DOCUMENTS

| Re. 29,687 | 7/1978 | Sertich | 433/120 |
| 2,960,314 | 11/1960 | Bodine | 433/118 |

FOREIGN PATENT DOCUMENTS

| 30-336399 | 3/1955 | Japan | 433/120 |
| 56-166842 | 12/1981 | Japan | 433/120 |

Primary Examiner—Robert Peshock
Attorney, Agent, or Firm—Ladas & Parry

[57] ABSTRACT

An air-driven dental scaler is provided with a vibrator assembly which comprises a rigid vibrator body having an inner disk-like chamber in which a disk-like rotor is received with a small gap between it and the chamber. The vibrator body is provided with a plurality of inlet ports which are arranged in such a manner that a jet of air impinges upon the cylindrical outer surface of the rotor in a substantially tangential direction to cause the rotor to rotate. As the rotor rotates, it strikes or rolls on the side walls of the chamber to impart a vibratory movement to the vibrator body, which movement is transmitted through a shaft to a scaler tip. The air leaves the chamber through an exhaust port provided, preferably, in one of the side walls of the chamber. The rotor is, preferably, provided with a central opening to enhance the exhaust efficiency.

17 Claims, 15 Drawing Figures

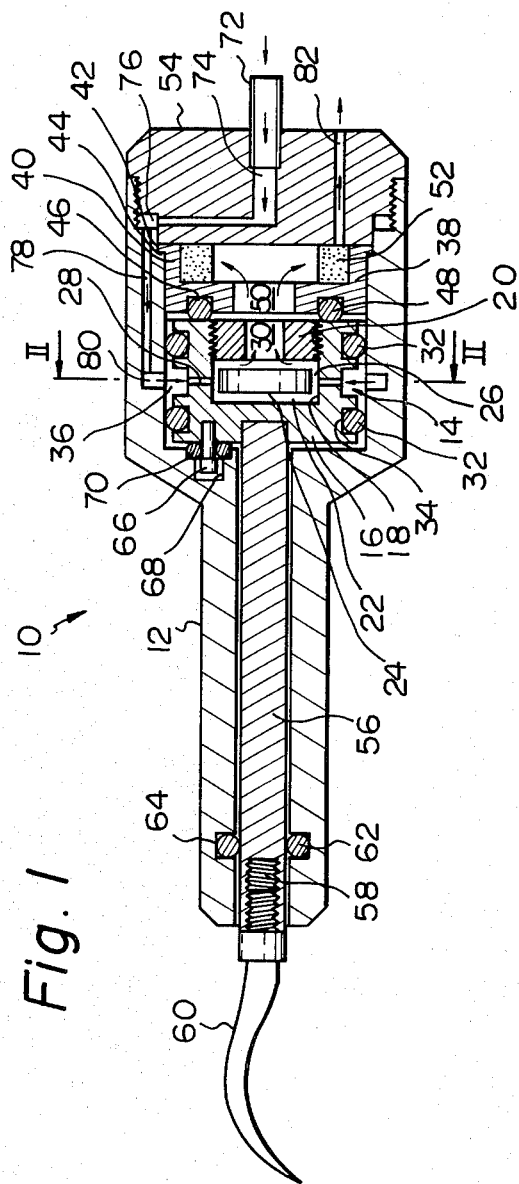
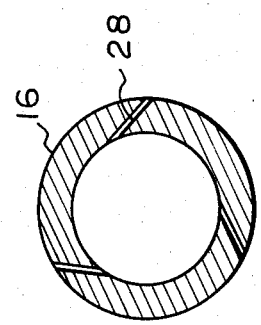
Fig. 1
Fig. 2

DENTAL SCALER

FIELD OF THE INVENTION

This invention relates to an air driven dental scaler for removing calculus or plaque from teeth.

DESCRIPTION OF THE PRIOR ART

Various types of powered dental scalers are known, among which there is a dental scaler provided with a solid-state ultrasonic transducer. An example of such an ultrasonic dental scaler is described in Japanese Patent Publication No. 6399/1958. The disadvantages of the ultrasonic dental scaler are that it requires complicated electronic components for controlling the frequency of vibration, causing the production cost to be prohibitive and that it requires cooling system for the transducer.

An air driven dental scaler is disclosed in Japanese Patent Application Laid-Open Publication No. 166842/1981 which comprises an air turbine having an output shaft, and means for transforming the rotational movement of the shaft to a cyclic oscillatory movement. This scaler is mechanically complex and has a lot of moving parts which are liable to wear.

Another type of air driven dental scaler is described in U.S. Pat. Re. No. 29,687 to Sertich. This scaler includes a sleeve-like rotor mounted rotatably around a shaft provided with outlet ports, the axis of which is offset at a distance from the longitudinal axis of the shaft. A jet of air ejected from the outlet ports strikes the inner wall of the rotor to urge it to rotate about the shaft. However, the sleeve-like rotor is thin-walled and, thus, is apt to break during operation.

SUMMARY OF THE INVENTION

An object of the invention is to provide an air driven dental scaler having a vibrator with a minimum of moving parts.

Another object of the invention is to provide an air driven dental scaler low in cost.

A further object of the invention is to provide an air driven dental scaler which has a long service life.

According to one aspect of the invention, there is provided a vibrator which comprises a substantially rigid vibrator body having a chamber therein defined by a cylindrical peripheral wall and a pair of parallel flat side walls perpendicular thereto, the distance between said side walls being smaller than the inner diameter of the peripheral wall, so that said chamber has a disk-like shape, said body having at least an exhaust port opening from said chamber on at least one of said side walls; a rotor received freely within said chamber and having a cylindrical peripheral surface and a pair of opposite side surfaces facing, respectively, said peripheral and side walls of the chamber, the diameter of said cylindrical surface being slightly smaller than the inner diameter of said cylindrical wall, so as to form a gap therebetween during operation of the vibrator, and; means for ejecting a flow of gaseous working fluid under pressure on said cylindrical peripheral surface of the rotor in a direction substantially tangential to said peripheral surface to cause said rotor to rotate within the chamber. Throughout the specification and the appended claims, the term "substantially tangential" is intended to mean not only a condition in which a line coincides with a tangent to a circle, but also a condition in which a line lies at a distance from the tangent to a larger or lesser degree. As the rotor rotates with its cylindrical peripheral surface spaced by said gap from the inner cylindrical wall of the chamber, a vibratory or oscillatory movement is produced on the vibrator body. Although the manner in which vibration or oscillation is generated as a result of the rotation of the rotor is not entirely clear to the inventor, it is presumed that during rotation the edges of the rotor alternately strike each of the flat side walls of the chamber one after another or that the rotor rolls on one or both of the side walls with its edges in contact therewith, thereby exerting to the walls an axial thrust, the point of action of which is located offset from the axis of the chamber and which turns around the axis as the rotor rotates, such axial thrust imparting a vibratory or oscillatory movement to the vibrator body. This striking or rolling action of the rotor, which takes place simultaneously with the rotation, can be proven by the fact that after operation of the vibrator for a certain period of time, a circular wear print is formed on the respective side walls of the chamber due to contact by the rotor edges.

With this arrangement, the rotor is only one moving part of the vibrator. The rotor has a disk-like configuration which is mechanically strong. Thus, a simple robust vibrator is obtained which is capable of being manufactured at a low cost.

Preferably, the exhaust port is provided on one of the side walls and the rotor is provided with a central through-opening to enable the working fluid to pass therethrough and exit toward said exhaust port.

The side surfaces of the rotor may be flat. Alternatively, the thickness of the rotor may be reduced toward its edges to hold them spaced from the side wall during the rest position of the rotor, so that when the vibrator is to be re-energized, a portion of the working fluid is forced to flow into said space to lift the rotor from the side wall, thereby making it easy to put the rotor into rotation again.

According to another aspect of the invention, there is provided a vibrating device which comprises a hollow casing; a vibrator; said vibrator comprising (a) a substantially rigid vibrator body having a disk-like chamber defined by a cylindrical peripheral wall and a pair of flat side walls perpendicular thereto, said body having at least an exhaust port opening from said chamber on at least one of said side walls, (b) a rotor received within said chamber and having a cylindrical peripheral surface and a pair of opposite side surfaces facing, respectively, said peripheral and side walls of the chamber, the diameter of said cylindrical surface being slightly smaller than the inner diameter of the cylindrical wall to form a gap therebetween when the device is operated, and, (c) means for blowing a jet of gaseous working fluid on the cylindrical surface of the rotor tangentially thereto to cause the rotor to rotate within the chamber with the cylindrical surface of the rotor being spaced by said gap from said cylindrical wall, but with the edges of the rotor in contact with or striking said flat side walls, thereby imparting a vibratory movement to the vibrator body; means for resiliently supporting said vibrator within said hollow casing, and; means rigidly connected at an end to said vibrator body and engageable at the other end with a work piece so that the vibratory movement is transmitted to the work piece.

According to a further aspect of the invention, there is provided a pneumatic vibratory tool which comprises an elongated hollow handpiece; a vibrator; said vibrator comprising (a) a substantially rigid vibrator body having a chamber defined by a cylindrical wall and a pair of opposite parallel side walls perpendicular thereto, the distance between said side walls being smaller than the inner diameter of said cylindrical wall so that said chamber is formed in a disk-like fashion, said body having at least an exhaust port provided on at least one of said side walls and communicating said chamber to the exterior of the vibrator body, (b) a rotor received freely within said chamber and having a cylindrical peripheral surface and a pair of opposite side surfaces corresponding, respectively, to said peripheral and side walls of the chamber, the diameter of said cylindrical surface being slightly smaller than the inner diameter of said cylindrical wall, so as to form a gap between said cylindrical wall and surface when the vibratory tool is energized, and, (c) means for supplying streams of compressed air on the cylindrical surface of the rotor in a direction substantially tangential to said surface to cause the rotor to rotate with its cylindrical surface being spaced by said gap from the cylindrical wall of the chamber, but with its peripheral edges rolling on or striking said side walls, thereby imparting a vibratory movement to the vibrator body; and an output shaft having a first end and a second end, said first end being rigidly connected to said vibrator body for operatively transmitting vibrations to said second end; means for resiliently supporting said vibrator and said output shaft within said hollow handpiece, and; a work tool mounted at the second end of the output shaft.

According to still another aspect of the invention, there is provided an air-driven dental scaler which comprises an elongated hollow handpiece; a vibrator; said vibrator comprising (a) a substantially rigid vibrator body having a chamber defiend by a cylindrical peripheral wall and a pair of parallel flat side walls perpendicular thereto, the distance between said side walls being smaller than the inner diameter of said peripheral wall so that said chamber has a disk-like shape, said body having at least an exhaust port provided in one of said side walls, (b) a disk-like rotor received freely within said chamber and having a cylindrical peripheral surface and a pair of opposite side surfaces, the diameter of said cylindrical surface being slightly smaller than the inner diameter of said cylindrical wall, so as to form a gap between said cylindrical wall and the surface during operation of the scaler, and, (c) means for directing a jet of compressed air substantially tangentially to said cylindrical peripheral surface of the rotor to cause said rotor to rotate within said chamber, with the peripheral surface thereof being spaced by said gap from the opposite cylindrical wall of the chamber and with the circumferential edges thereof in contact with or in striking relationship with said side walls of the chamber, thereby imparting a vibratory movement to said rotor body; a shaft connected at an end to said vibratorbody; means for resiliently supporting said vibrator and said shaft within said elongated handpiece for vibratory movement with respect to the handpiece, and; a scaler tip mounted detachably at the other end of the shaft.

The means for directing a jet of compressed air preferably comprises a plurality of air inlet ports provided in said vibrator body on a plane perpendicular to the axis of the chamber and spaced at an angularly equal distance from each other, said inlet ports opening into said chamber in a direction substantially tangential with respect to the outer periphery of the rotor when energized.

The rotor may has a central through-aperture for allowing the air between the other side wall and the rotor surface to be exhausted smoothly toward the exhaust port.

The edges of the rotor may be tapered or chamfered, so that the rotor is readily lifted from the side wall of the chamber and is put into rotation when the dental scaler is energized after pause.

BRIEF DESCRIPTION OF THE DRAWINGS

FIG. 1 is a schematic side elevational view, partly in section, of a dental scaler according to the invention;

FIG. 2 is a transversal cross-sectional view of a vibrator body along the line II—II of FIG. 1;

DESCRIPTION OF THE PREFERRED EMBODIMENTS

Figure 3:
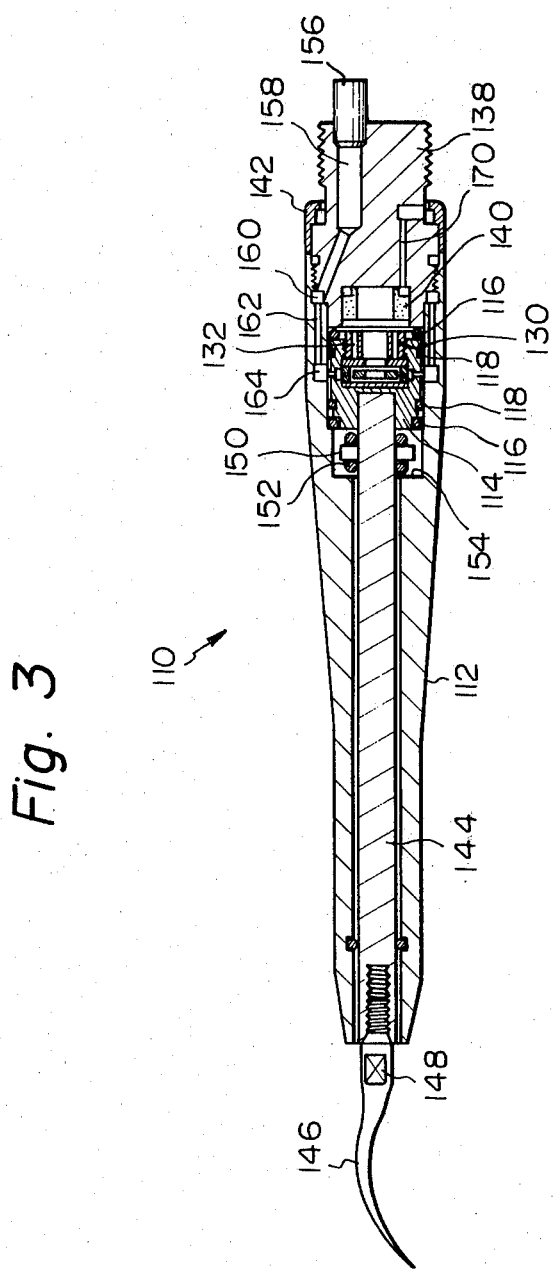
FIG. 3 is a schematic side elevational view, partly in section, of another embodiment of the dental scaler according to the invention.

Referring to FIG. 1, an air-driven dental scaler, generally indicated by reference numeral 10, comprises an elongated handpiece 12 which has a longitudinal stepped bore. The larger bore of the handpiece 12 receives a vibrator assembly, indicated generally by reference numeral 14, which includes a vibrator body 16 having a cylindrical blind bore 18. A side plate 20 is screwed into the vibrator body 16 to close the bore 18, in such a manner that a disk-like chamber 22 is formed within the vibrator body 16. The chamber 22 receives a disk-like rotor 24, the outer diameter of which is slightly smaller than the diameter of the inner circumferential wall of the chamber 22, so as to form a gap 26 between the outer wall of the rotor 24 and the inner wall of the chamber 22 when the rotor 24 is put into rotation, as described hereinafter.

The vibrator body 16 is provided with a plurality of inlet ports, which are shown schematically in FIG. 1 by reference numeral 28. As shown in FIG. 2, these inlet ports 28 are spaced apart from each other at an equal angular distance, each inlet port 28 having an axis which is substantially tangential with respect to the cylindrical peripheral wall of the rotor when the rotor is rotated.

The side plate 20 is provided with a central opening 30 which forms an exhaust port for the chamber 22.

A pair of O-rings 32 are mounted air-tightly between the larger bore of the handpiece 12 and a pair of annular grooves 34 formed on the outer periphery of the vibrator body 16. These O-rings 32 serve, on the one hand, to resiliently support the vibrator assembly 14 within the handpiece 12 and, on the other hand, to form an annular air plenum 36 around the inlet ports 28.

A back plate 38 is loosely fitted within the larger bore of the handpiece 12 at the rear of the vibrator assembly 14. This back plate 38 has a skirt 40 provided with a flange 42 which abuts against a shoulder 44 formed on the larger bore to limit the leftward movement of the back plate 38 relative to the handpiece 12. The back plate 38 is provided on a side thereof with an annular groove 46 in which an O-ring 48 is mounted. This O-ring 48 is urged by said plate 38 against the vibrator body 16 to resiliently hold the latter, as well as to prevent the air from leaking radially outwardly through the clearance between the body 16 and plate 38. The back plate 38 is provided with a central opening 50 for exhausing the air from the exhaust port 30. A silencer ring 52, made from sintered metal, is mounted within the back plate 38. An end plug 54 is screwed into the internally threaded end of the handpiece 12, so that the back plate 38, as well as the silencer ring 52, are held in place.

A shaft 56 is rigidly secured to the vibrator body 16. The free end of the shaft 56 is provided with an internally threaded hole 58 into which a threaded end of a scaler tip 60 is screwed. An O-ring 62 is mounted between a groove 64 formed on the smaller bore of the handpiece and the shaft 56 to resiliently support the shaft with respect to the handpiece 12.

A stud or pin 66 is rigidly mounted to a side of the vibrator body 16. The stud 66 extends parallel to the shaft 56 to project into a stepped cylindrical recess 68, which is formed on the inner transversal wall of the handpiece in alignment with the stud 66. An O-ring 70 is mounted around the stud 66 between the recess 68 and the vibrator body 16. The O-ring 70, seated on a shoulder of the recess 68, acts to resiliently support the vibrator body in the axial direction. The O-ring 70 resiliently engages the stud 66 and also serves to prevent the vibrator assembly from being rotated during operation of the dental scaler or when a rotational torque is applied to the shaft 56, such as occurs when the scaler tip 60 is screwed into the threaded hole 58.

The end plug 54 is provided with a hose coupling 72 for connecting a compressed air supply hose, not shown, and with an air passage 74 which opens into an annular space 76 formed between the bore of the handpiece 12 and the circumferential surface of the end plug 54. The annular space 76 is communicated through an air passage 78 to an annular passage 80 which opens into the air plenum 36.

An exhaust passage 82 is formed in the end plug 54 for exhausting the air from the silencer to the exterior of the dental scaler.

In operation, an air supply hose from a dental unit is connected to the hose coupling 72 and the compressed air, having a gauge pressure of about 3 Kg/cm$^2$, is fed through air passages 74, 76, 78 and 80 to the air plenum 36, as shown by arrows. The air flows through the inlet ports 28 into the chamber 22 in the form of an air jet that impinges upon the outer surface of the rotor 24 in a substantially tangential direction, producing a vortex or swirl in the chamber. As a result, the rotor starts to rotate with its outer peripheral surface spaced by a small gap from the inner circumferential wall of the chamber, due to an air cushion formed therein.

The rotational movement of the rotor involves some fluttering, flapping or oscillating movement of the rotor, causing a vibratory or oscillatory movement of the vibrator body. I am not thoroughly aware as to why and how such a vibratory or oscillatory movement is produced on the vibrator body due to the rotation of a disk-like rotor within a narrow chamber. However, I have observed, in a prototype of my vibrator provided with a transparent side wall for viewing, that the rotor oscillatorily rotates, like a coin spinning on a table begins to roll on the table with its edge alternately striking the table surface as its rotational speed becomes lowered. I have also observed that, after operation of my vibrator for a certain period of time, a circular wear print is formed on each inner side wall of the chamber. This implies that during rotation of the rotor, the edges thereof alternately strike each of the two side walls of the chamber one after another, thereby imparting a vibratory movement to the vibrator body. This also implies that, in combination with or independent from the striking action of the rotor, the rotor rolls on one or both of the chamber side walls with its edges in contact therewith, so that an axial thrust is applied to the side walls at the point of contact, which is offset from the axis of the chamber and turns around in response to the rotor rotation. These striking and/or rolling actions of the rotor impart a vibratory or oscillatory movement to the vibrator body.

The vibration of the vibrator body is transmitted through the shaft 56 to the scaler tip 60 which removes calculus or plaque from teeth.

The air in the chamber is exhausted through openings 30 and 50 to pass the silencer ring 52 and is discharged through the exhaust passage 82.

The frequency of vibration may be regulated by varying the pressure of compressed air. By augmenting the pressure, the flow rate of air is increased, which in turn increases the rotational speed of the rotor, whereby the frequency is enhanced.

For practical purposes of the scaling operation, the frequency of vibration, as measured at the foremost end of the scaler tip, may vary from 3,000 to 20,000 cycles per second. The lower limit is determined by the minimum efficiency of the scaler. The upper limit depends on two opposing factors: (1) as the frequency increases to approach the untrasonic range, the noise produced by the scaler becomes inaudible to the dentist and the patient, thereby enabling a comfortable operation to be performed; (2) as the scaler tip vibrates at a very high frequency, it is liable to damage the surface of the teeth. It was possible to obtain a frequency on the order of about 6,000 cycles per second using compressed air having a pressure of about 3 kg/cm$^2$, when the chamber of the vibrator was about 1.8 mm in width and about 7 mm in diameter, and the rotor was about 1.1 mm in thickness and about 6.5 mm in diameter. It will be apparent that the frequency may be increased by augmenting the pressure of the compressed air.

Figure 4A:
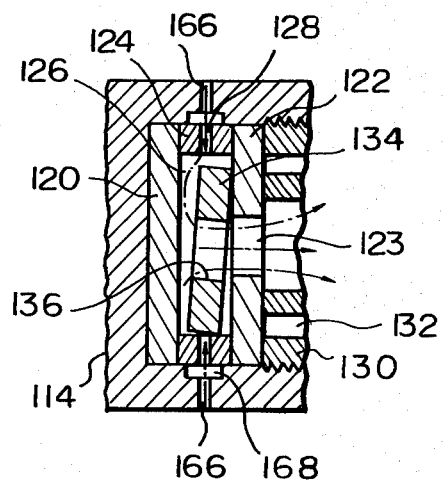
FIGS. 4A and 4B are partial views, in cross-section, of the vibrator assemblies having rotors with and without a central through-aperture, respectively.

Referring to FIGS. 3 and 4A, there is shown another embodiment of the dental scaler according to the invention. The dental scaler 110 includes a handpiece 112 in which a vibrator body 114 is resiliently supported by a pair of O-rings 116, providing axial support, and another pair of O-rings 118, providing radial support. The vibrator body 114 has a blind bore in which a pair of side plates 120 and 122 are mounted spaced by a spacer ring 124 to form a chamber 126 as shown enlarged in FIG. 4A. The spacer ring 124 is provided with a plurality of air inlet ports 128, similar to those in the preceding embodiment. The side plate 122 is provided with an exhaust port 123 at its center. The side plates 120 and 122 and spacer ring 124 are tightly held together by a backup ring 130 screwed into the threaded bore of the vibrator body 114. The backup ring 130 is provided with a pair of pin holes 132 in which the pins of a spanner engage therein for the assembly of the vibrator.

A rotor 134 which has a central through aperture 136, the function of which will be described later in more detail, is placed in the chamber 126.

An end plug 138, provided with a silencer ring 140, is screwed into the threaded bore of the handpiece until it abuts against the outer O-ring 116 and holds the vibrator body 114 in place within the handpiece. An end cap 142 is attached to the end plug 138 adjacent to the rear end of the handpiece.

A shaft 144 is rigidly connected at an end to the vibrator body 114, the other end of the shaft being threadingly connected to a scaler tip 146. The scaler tip is provided with a pair of opposite flat surfaces, one of which is shown in the drawing and indicated by reference numeral 148. These flat surfaces are intended to be engaged by an open ended spanner during mounting and dismounting of the scaler tip.

A stud or pin 150 is mounted perpendicular to the shaft 144 and a pair of O-rings 152 are provided around the pin 150, one at each end thereof. These O-rings 152 are adapted to engage the longitudinal inner wall of a cylindrical recess 154 extending coaxially with the pin 150, so as to prevent the shaft from rotating with respect to the handpiece.

The compressed air is fed through a hose coupling 156, an air passage 158 in the end plug 138, an annular space 160 formed between the handpiece and the end plug, an air passage 162 in the handpiece, an annular space 164 and a plurality of radially extending air passages 166 to an air plenum 168. The air in the chamber 126 is exhausted via the central openings of the side plate 122 and the backup ring 130, the silencer 140, an exhaust passage 170 and a gap formed between the inwardly turned flange of the end cap 142 and the outer periphery of the end plug 138.

Figure 4B:
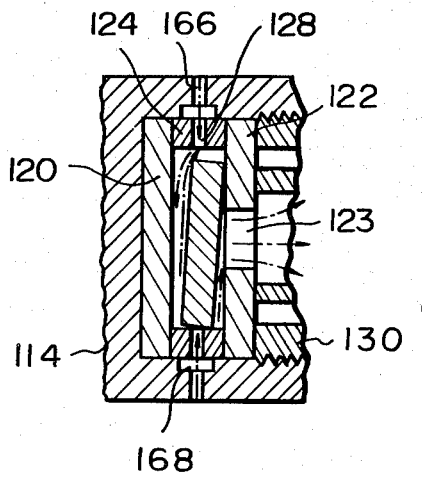

In operation, after rotating the rotor, the portion of the air that flowed into the space between the side plate 120 and the rotor 134 is vented smoothly through the central aperture 136 toward the exhaust opening of the side plate 122, as shown by chain lines in FIG. 4A. This increases the exhaust efficiency of the vibrator and enables a higher frequency of vibration to be obtained. This will be readily understood by comparison with a vibrator having a rotor without a central aperture, as shown in FIG. 4B. In the vibrator of FIG. 4B, the portion of the air flowing into that space is subjected to the counteraction of the air flowing radially outwardly and, thus, air exhaust is hindered.

Figures 5A, 5B, 5C, 5D:
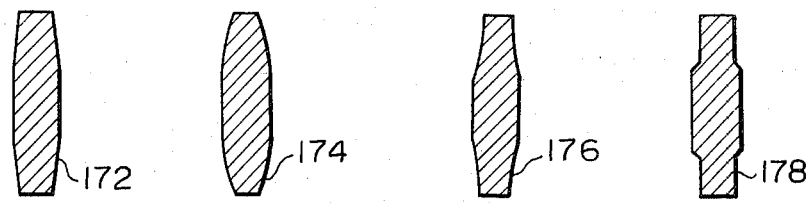
FIGS. 5A to 5H are cross-sectional views showing various versions of the rotor.
Figures 5E, 5F, 5G, 5H:
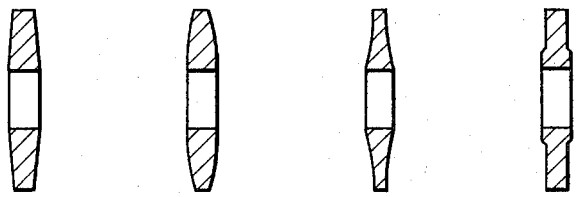

Referring to FIGS. 5A through 5H, various versions of the cross-section of the rotor are shown. Throughout these embodiments, the thickness of the rotor is reduced toward the peripheral surface. In the embodiment of FIG. 5A, the peripheral portion of the rotor is tapered, as shown, by the inclined flat surfaces 172. In the embodiment of FIG. 5B, the rotor thickness is reduced from the center toward the periphery of the rotor along outwardly curved annular surface portions 174. In FIG. 5C, the side surfaces of the rotor are cut partly away, to form concave surfaces 176. FIG. 5D illustrates an embodiment which has stepped surfaces 178. FIGS. 5E through 5H illustrate examples similar to those of FIGS. 5A through 5D, but in which a central through aperture is provided.

Figure 6A:
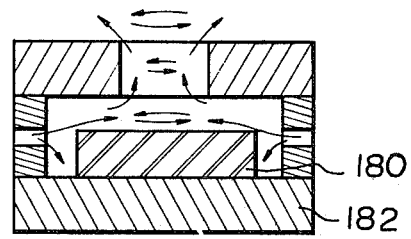
FIGS. 6A and 6B are partial views, in cross-section, of the vibrator assemblies having, respectively, a rotor with flat side surfaces and a rotor with a tapered edge.
Figure 6B:
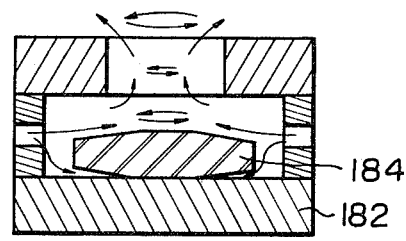

Reduction of the peripheral thickness of the rotor is advantageous for the following reasons. With a rotor 180 defined by flat side surfaces, the rotor rests on the flat inner wall of the side plate 182 in intimate contact therewith, as illustrated in FIG. 6A, during a pause of the operation, when the dental scaler is held in a vertical position by being hanged from the dental unit. In that event, the rotor 180 is likely to stick to the side plate 182 due to a film of air-born lubricating oil or moisture deposited on the inner wall of the side plate, so that the rotor is not put into rotation when the air supply is reopened to energize the vibrator. To the contrary, with a rotor 184 having tapered or chamfered edge, a portion of the air will flow into the space between the side plate and rotor, as shown in FIG. 6B, and cause the latter to be lifted from the plate, thereby facilitating the initial rotation of the rotor. By reducing the peripheral thickness of the rotor, it is possible to put the vibrator into operation regardless of the rest position of the dental scaler.

While the present invention has been described herein with reference to specific embodiments thereof, it is contemplated that considerable variations may be made in the construction of the parts within the spirit and scope of the appended claims.

For example, more than two series of inlet ports may be provided, each series being spaced from one another in the axial direction.

Further, the side plate may be provided with more than two exhaust ports arranged at a distance from the axis of the chamber.

I claim:
1. A vibrator comprising:
a substantially rigid vibrator body having a chamber therein defined by a cylindrical peripheral wall and a pair of parallel flat side walls perpendicular thereto, the distance between said side walls being smaller than the inner diameter of said cylindrical peripheral wall, so that said chamber has a disk-like shape, said body having at least an exhaust port opening from said chamber on at least one of said side walls;
a rotor received freely within said chamber, said chamber being substantially of greater height than said rotor, said rotor having a cylindrical peripheral surface and a pair of opposite side surfaces facing, respectively, said peripheral and side walls of the chamber, the diameter of said cylindrical surface being slightly smaller than the inner diameter of said cylindrical wall, so as to form a gap therebetween during operation of the vibrator, and;
means for ejecting a flow of gaseous working fluid under pressure on said cylindrical peripheral surface of the rotor in a direction substantially tangential to said surface, adequate to cause said rotor to rotate within said chamber with its cylindrical surface spaced by said gap from the cylindrical wall of the chamber, but with its edges in contact with or striking said flat side walls, thereby imparting a vibratory movement to said vibrator body.

2. A vibrator according to claim 1, wherein said exhaust port is provided on one of the side walls and wherein said rotor has a central through-aperture for enabling the working fluid, which is located between the other side wall and the rotor, to exhaust smoothly therethrough toward said exhaust port.

3. A vibrator according to claim 2, wherein said side surfaces of the rotor are flat.

4. A vibrator according to claim 2, wherein the thickness of the rotor is reduced toward the edges thereof to hold the edges spaced from the side wall of the chamber when the vibrator is not being operated, so that when the vibrator is to be re-energized, a portion of the working fluid flows into said space to lift the rotor from the side wall, thereby making it easy to put the rotor into rotation.

5. A vibrating device comprising:
a hollow casing;
a vibrator, said vibrator comprising,
(a) a substantially rigid vibrator body having a disk-like chamber defined by a cylindrical peripheral wall and a pair of parallel flat side walls perpendicular thereto, said body having at least an exhaust port opening from said chamber on at least one of said side walls,
(b) a rotor received within said chamber, said chamber being substantially of greater height than said rotor, said rotor having a cylindrical peripheral surface and a pair of opposite side surfaces facing, respectively, said peripheral and side walls of the chamber, the diameter of said cylindrical surface being slightly smaller than the inner diameter of said cylindrical wall to form a gap therebetween when the device is being operated, and,
(c) means for blowing a jet of gaseous working fluid on said cylindrical surface of the rotor tangentially thereto adequate to cause said rotor to rotate within said chamber, with the cylindrical surface of the rotor spaced by said gap from said cylindrical wall, but with the edges thereof in contact with or striking said flat side walls, thereby imparting a vibratory movement to said vibrator body;
means for resiliently supporting said vibrator within said hollow casing, and;
means rigidly connected at an end to said vibrator body and engageable at the other end with a work piece for transmitting vibratory movement to a work piece.

6. A vibrating device according to claim 5 having a vibrator as claimed in claim 2, 3, 4 or 5.

7. A pneumatic vibratory tool comprising:
an elongated hollow handpiece;
a vibrator, said vibrator comprising
(a) a substantially rigid vibrator body having a chamber defined by a cylindrical wall and a pair of opposite parallel side walls perpendicular thereto, the distance between said side walls being smaller than the inner diameter of said cylindrical wall, so that said chamber is formed in a disk-like fashion, said body having at least an exhaust port provided on at least one of side walls and communicating said chamber to the exterior of the vibrator body,
(b) a rotor received freely within said chamber, said chamber being substantially of greater height than said rotor, said rotor having a cylindrical peripheral surface and a pair of opposite side surfaces corresponding, respectively, to said cylindrical and side walls of the chamber, the diameter of said cylindrical surface being slightly smaller than the inner diameter of said cylindrical wall, so as to form a gap between said cylindrical wall and said surface when the vibratory tool is energized, and,
(c) means for supplying streams of compressed air on the cylindrical surface of the rotor in a direction substantially tangential to said surface adequate to cause said rotor to rotate with its cylindrical surface spaced by said gap from the cylindrical wall of the chamber, but with its peripheral edges rolling on or striking said side walls, thereby imparting vibratory movement to said vibrator body;
an output shaft having a first end and a second end, said first end being rigidly connected to said vibrator body for operatively transmitting vibrations to said second end;
means for resiliently supporting said vibrator and said output shaft within said hollow handpiece, and;
a work tool mounted at the second end of the output shaft.

8. A pneumatic vibratory tool according to claim 7 having a vibrator as claimed in claim 2, 3, 4 or 5.

9. An air-driven dental scaler comprising:
an elongated hollow handpiece;
a vibrator;
said vibrator comprising,
(a) a substantially rigid vibrator body having a chamber defined by a cylindrical peripheral wall and a pair of parallel flat side walls perpendicular thereto, the distance between said side walls being considerably smaller than the inner diameter of said peripheral wall, so that said chamber has a disk-like shape, said body having at least an exhaust port provided in one of said side walls,
(b) a disk-like rotor received freely within said chamber, said chamber being substantially of greater height than said rotor and said rotor having a cylindrical peripheral surface and a pair of opposite side surfaces, the diameter of said cylindrical surface being slightly smaller than the inner diameter of said cylindrical wall, so as to form a gap between said cylindrical wall and surface during operation of the scaler, and,
(c) means for directing a jet of compressed air substantially tangentially to said cylindrical peripheral surface of the rotor, adequate to cause said rotor to rotate within said chamber, with the peripheral surface thereof spaced by said gap from the opposite cylindrical wall of the chamber and with the circumferential edges thereof in contact with or in striking relationship with said side walls of the chamber, thereby imparting a vibratory movement to said vibrator body;
a shaft connected at an end to said vibrator body;
means for resiliently supporting said vibrator and shaft for vibratory movement with respect to the handpiece, and;
a scaler tip mounted detachably at the other end of said shaft.

10. A dental scaler according to claim 9, wherein said rotor has a central through-aperture for allowing the air between the other side wall and the rotor to exhaust smoothly toward said exhaust port.

11. A dental scaler according to claim 10, wherein said means for directing a jet of compressed air comprises a plurality of air inlet ports provided in said vibrator body on a plane perpendicular to the axis of the chamber and spaced at an angularly equal distance with each other, said inlet ports opening into said chamber in a direction substantially tangential with respect to the outer periphery of the rotor when energized.

12. A dental scaler according to claim 11, wherein the thickness of the rotor is reduced toward the edges thereof such that the edges are spaced from the side wall of the chamber in the inoperative position of the rotor, so that when the vibrator is to be re-energized, a portion of the air flows into said space to lift the rotor from the side wall thereby making it easy to again put the rotor into rotation.

13. A dental scaler according to claim 12, wherein the peripheral portion of the rotor is tapered.

14. A dental scaler according to claim 12, wherein said edges are chamfered.

15. A dental scaler according to claim 12, wherein the thickness of the rotor is reduced from the center toward the periphery of the rotor along outwardly curved annular surface portions.

16. A dental scaler according to claim 12, wherein the side surfaces of the rotor are partly cut away to form concave surfaces.

17. A dental scaler according to claim 12, wherein the side surfaces of the rotor are stepped.

* * * * *